United States Patent
Hartley et al.

(10) Patent No.: US 7,715,903 B2
(45) Date of Patent: May 11, 2010

(54) GUIDE WIRE

(75) Inventors: David Ernest Hartley, Subiaco (AU); Frank Karhu Christiansen, Haslev (DK)

(73) Assignees: Cook Incorporated, Bloomington, IN (US); William Cook Europe APS, Bjaeverskov (DK); William A Cook Australia Pty., Ltd., Queensland (AU)

( * ) Notice: Subject to any disclaimer, the term of this patent is extended or adjusted under 35 U.S.C. 154(b) by 447 days.

(21) Appl. No.: 10/645,089

(22) Filed: Aug. 21, 2003

(65) Prior Publication Data

US 2004/0073141 A1 Apr. 15, 2004

Related U.S. Application Data

(60) Provisional application No. 60/405,161, filed on Aug. 22, 2002.

(51) Int. Cl.
*A61M 25/00* (2006.01)

(52) U.S. Cl. .................. 600/433; 600/434; 600/435; 600/585; 604/164.13

(58) Field of Classification Search .............. 600/585, 600/433–435, 164.13; 604/164.13
See application file for complete search history.

(56) References Cited

U.S. PATENT DOCUMENTS

| | | | | |
|---|---|---|---|---|
| 454,390 | A * | 6/1891 | Thornycroft | 122/491 |
| 3,906,938 | A * | 9/1975 | Fleischhacker | 600/585 |
| 4,538,622 | A * | 9/1985 | Samson et al. | 600/585 |
| 4,846,186 | A * | 7/1989 | Box et al. | 600/434 |
| 4,925,445 | A * | 5/1990 | Sakamoto et al. | 604/528 |
| 4,971,490 | A * | 11/1990 | Hawkins | 600/585 |
| 5,040,543 | A * | 8/1991 | Badera et al. | 600/585 |
| 5,295,493 | A * | 3/1994 | Radisch, Jr. | 600/585 |
| 5,345,937 | A * | 9/1994 | Middleman et al. | 600/434 |
| 5,363,847 | A * | 11/1994 | Viera | 600/434 |
| 5,365,943 | A * | 11/1994 | Jansen | 600/585 |
| 5,421,349 | A * | 6/1995 | Rodriguez et al. | 600/585 |
| 5,464,016 | A * | 11/1995 | Nicholas et al. | 600/463 |
| 5,584,803 | A * | 12/1996 | Stevens et al. | 604/6.16 |
| 5,662,621 | A * | 9/1997 | Lafontaine | 604/528 |
| 5,664,580 | A * | 9/1997 | Erickson et al. | 600/585 |
| 5,673,707 | A * | 10/1997 | Chandrasekaran | 600/585 |
| 5,693,083 | A * | 12/1997 | Baker et al. | 623/1.11 |
| 5,827,201 | A * | 10/1998 | Samson et al. | 600/585 |
| 5,924,998 | A * | 7/1999 | Cornelius et al. | 600/585 |
| 6,086,548 | A * | 7/2000 | Chaisson et al. | 600/585 |
| 6,165,140 | A * | 12/2000 | Ferrera | 600/585 |
| 6,254,550 | B1 * | 7/2001 | McNamara et al. | 600/585 |

(Continued)

*Primary Examiner*—Max Hindenburg
*Assistant Examiner*—Rene Towa
(74) *Attorney, Agent, or Firm*—Brinks Hofer Gilson & Lione

(57) ABSTRACT

A guide wire (1) to assist percutaneous endovascular deployment which has zones of varying stiffness. An elongate central zone (3) of high stiffness, a proximal zone (4) of transition from high stiffness to semi-stiffness and a distal zone (5) of transition from high stiffness to being relatively flexible. The distal zone (5) has three zones, a semi stiff zone (11) adjacent the central zone, a transition zone (13) being of flexibility of from semi-stiff extending to flexible and a tip zone (15) being of high flexibility. The distal tip has a small J curve (16) to ensure that it is atraumatic in vessels and to prevent damage to the aortic heart valve. The distal zone (5) can also have a large curve to assist with anchoring the guide wire into the aortic arch.

16 Claims, 6 Drawing Sheets

U.S. PATENT DOCUMENTS

| | | |
|---|---|---|
| 6,595,932 B2 * | 7/2003 | Ferrera .................. 600/585 |
| 6,716,183 B2 * | 4/2004 | Clayman et al. ............ 600/585 |
| 6,743,227 B2 * | 6/2004 | Seraj et al. ................ 606/41 |
| 6,761,696 B1 * | 7/2004 | Wong ..................... 600/585 |
| 7,025,734 B1 * | 4/2006 | Ellis et al. ................ 600/585 |
| 7,048,695 B1 * | 5/2006 | Schwager ................ 600/585 |
| 2002/0123698 A1 * | 9/2002 | Garibotto et al. .......... 600/585 |
| 2003/0083623 A1 * | 5/2003 | Berg et al. ............. 604/164.13 |
| 2003/0208141 A1 * | 11/2003 | Worley et al. ............. 600/585 |
| 2003/0233058 A1 * | 12/2003 | Ewers et al. ............. 600/585 |
| 2004/0019359 A1 * | 1/2004 | Worley et al. ............. 606/129 |
| 2004/0039304 A1 * | 2/2004 | Connors, III et al. ........ 600/585 |
| 2004/0039307 A1 * | 2/2004 | Ferrera .................. 600/585 |
| 2004/0073141 A1 * | 4/2004 | Hartley et al. ............. 600/585 |

* cited by examiner

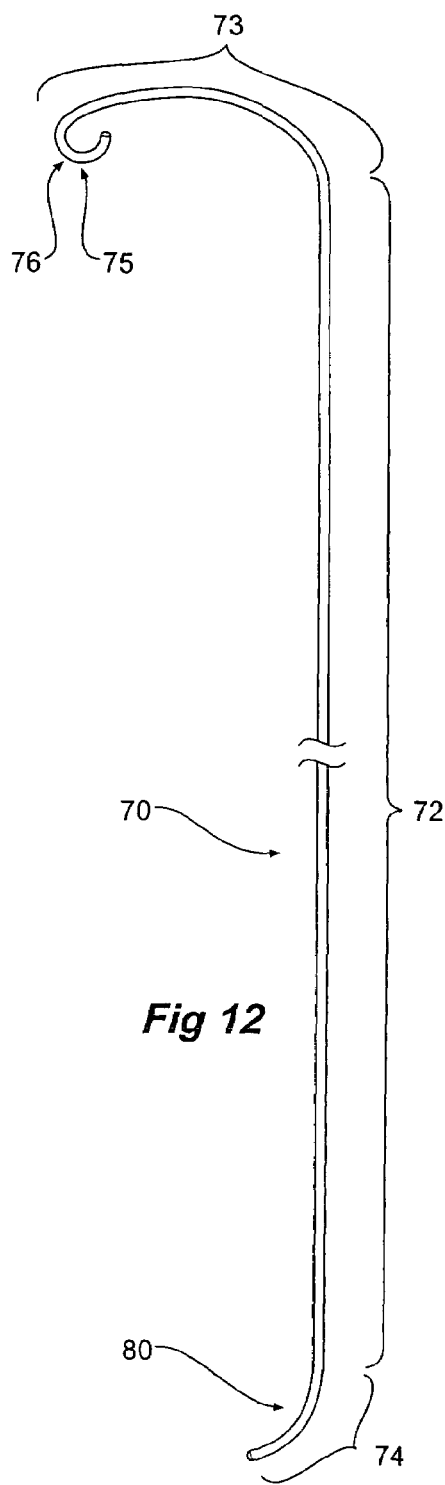
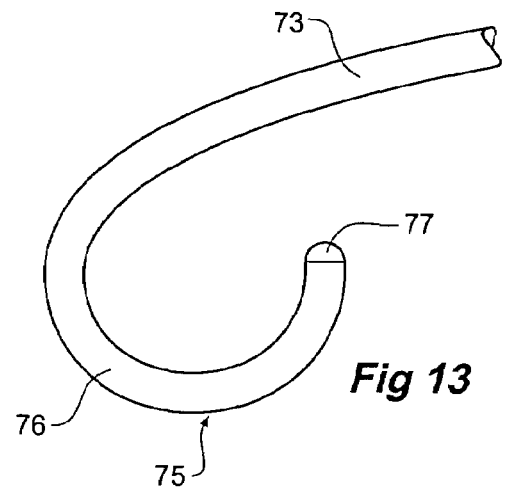
*Fig 13*
*Fig 12*
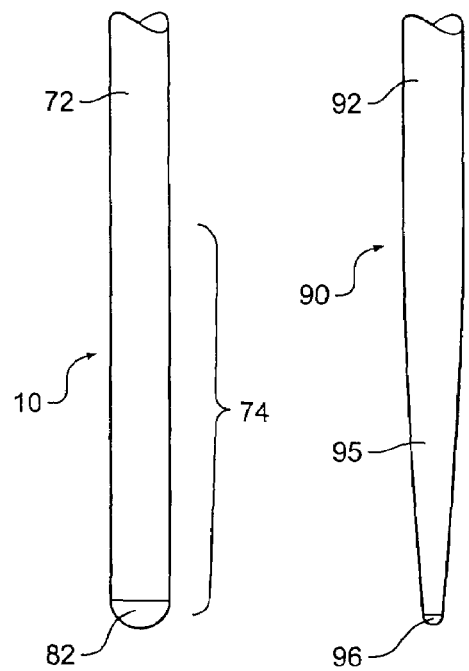
*Fig 14*     *Fig 15*

GUIDE WIRE

CROSS-REFERENCE TO RELATED APPLICATIONS

This application claims priority of provisional application Ser. No. 60/405,161, filed Aug. 22, 2002.

TECHNICAL FIELD

This invention relates to a guide wire for deploying an endovascular deployment device and particularly for deploying a stent graft into the thoracic arch region of the aorta.

BACKGROUND OF THE INVENTION

Use of the percutaneous entry technique for medical procedures has expanded rapidly over the last few years. Originally, percutaneous entry was used for the introduction of small, flexible catheters for diagnostic radiographic studies. The use of percutaneous entry rapidly expanded to therapeutic devices such as balloon angioplasty devices, occlusion devices and now to endovascular stent graft delivery.

In the percutaneous entry technique, guide wires are used to guide the catheter through a needle puncture site, into the vessel and up to a target anatomy. Guide wires, in general, are simple devices that will control or influence the direction and advancement of the catheter as it is advanced through the vessel. The guide wires currently available to interventionists are, for the most part, designed to lead small flexible catheter devices through the vasculature. Large, stiff devices such as endovascular stent graft devices, are not controlled or influenced by typical guide wires when they are placed percutaneously. Very stiff guide wires are typically used with these types of devices; however, the stiff wires tend to be much stiffer than the vessels and will not traverse the vasculature easily. In addition, it frequently traumatizes the vessel walls.

In addition, the proximal ends of very stiff wires can damage or become lodged in the walls of the guide wire lumen of a delivery system.

The guide wires currently used for this type of procedure are multipurpose "heavy duty" guide wires. These guide wires do not have the characteristics to solve the problems of percutaneous deployment of large stiff devices.

The "double ended" guide wires available from Cook Inc., Bloomington Ind., are designed so that either end can be the distal end of the guide wire. One end may have a "J" curved distal end and the other end may be straight. This allows the physician the option to use either type distal end without using an additional guide wire. Again these guide wires do not have the characteristics to solve the problems of percutaneous deployment of large stiff devices.

The guide wire described in U.S. Pat. No. 6,254,550, to McNamara, et. al, does not possess the needed stiffness transitions nor the correct shape. The guide wire described in U.S. Pat. No. 6,001,068 to Uchino, et. al., does not have the combinations of flexibilities located in the curves so as to make the guide wire lock or anchor in place in the anatomy. In addition, this patent does not teach the use of a stiffness transition on the proximal end to protect the devices being used with the guide wire.

Throughout this specification the terms proximal and distal should be understood as being in the terms of a physician using the guide wire. Hence the term distal means that portion of the guide wire which in use is farthest from the physician and the term proximal means the portion of the guide wire which is nearest to the physician.

SUMMARY OF THE INVENTION

It is the object of this invention to provide a guide wire which will overcome at least some of these problems or at least provide the physician with a useful alternative.

In one form although this may not be the only or broadest form the invention is said to reside in a guide wire to assist percutaneous endovascular deployment; the guide wire having zones of varying stiffness comprising; an elongate central zone of high stiffness; a proximal zone of transition from high stiffness to semi-stiffness; and a distal zone of transition from high stiffness to being relatively flexible.

Preferably the distal zone comprises three zones being a semi stiff zone adjacent the central zone; a transition zone being of flexibility of from semi-stiff extending to flexible; and a tip zone being of high flexibility.

Preferably the central zone comprises a stainless steel central mandrel of substantially constant diameter along its length.

Preferably the proximal zone comprises a tapered mandrel as an extension of the central mandrel with a proximal wire coil on and extending along the tapered mandrel.

In one arrangement the proximal coil may be of substantially constant coil diameter or alternatively the proximal coil may be tapered.

Preferably the proximal wire coil is laser welded to the tapered mandrel and the proximal wire coil terminates in a rounded tip.

In an alternative arrangement the distal zone can comprise in order from the central zone, a tapered mandrel portion and a portion of constant reduced diameter with a distal wire coil on and extending along the tapered mandrel portion and the portion of constant reduced diameter.

Preferably the distal coil is of substantially constant coil diameter.

Preferably the distal wire coil is laser welded to the tapered mandrel portion and the distal wire coil terminates in a rounded tip.

Preferably the distal end of the guide wire has a distal curve with a radius of curvature of from 50 to 150 mm and preferably about 90 mm and wherein the distal curve includes a portion of the central zone, the semi stiff zone adjacent the central zone and a portion of the transition zone.

The tip zone may have a tip curve with a radius of curvature of from 5 to 20 mm and preferably about 10 mm.

In an alternative form the invention comprises a guide wire to assist percutaneous endovascular deployment comprising; a mandrel of substantially constant diameter along its length in a central zone, a proximal portion of the mandrel having a proximal tapered portion with a proximal wire coil on and extending along the proximal tapered portion, a distal portion of the mandrel comprising in order from the central zone, a distal tapered portion and a portion of constant reduced diameter with a distal wire coil on and extending along the distal tapered portion and the portion of constant reduced diameter.

Preferably the diameter of the mandrel in the central zone, the coil diameter of the proximal wire coil and the coil diameter of the distal wire coil are of substantially equal.

The central zone, the proximal wire coil and the distal wire coil may be coated with polytetrafluoroethylene (PTFE).

In an alternative form the invention resides in a guide wire for a medical device, the guide wire having a proximal end and a distal end and being of a type which is relatively stiff intermediate the distal end and the proximal end and having more flexible proximal and distal tips.

Preferably the more flexible proximal and distal tips are tapered towards their respective ends to facilitate deployment.

There may be further including a pre-formed bend adjacent the distal end to assist with deployment of the deployment device into portions of the vasculature which are already curved such as the thoracic arch and the distal tip may be formed into a part circular shape or pigtail to assist with preventing damage to vasculature as the device is deployed.

At least some portions of the guide wire may be radio-opaque to assist with visualisation of deployment and especially the distal tip may be radiopaque.

In an alternative form the invention resides in a guide wire for assisting the deployment of an endovascular device, the endovascular device having a guide wire catheter through which the guide wire is inserted in use, the guide wire having a proximal end and a distal end and being relatively stiff intermediate the distal end and the proximal end, the guide wire having more flexible proximal and distal tips, a pre-formed bend adjacent the distal end to assist with deployment of the deployment device into portions of the vasculature which are already curved such as the thoracic arch, the distal tip being formed into a part circular shape or pigtail to assist with preventing damage to vasculature as the device is deployed and the proximal tip being formed into a rounded shape to assist with insertion through the guide wire catheter of the endovascular device.

It will be seen that by this invention there is provided a guide wire that has the body or stiffness needed to control large diameter, stiff devices but still not damage the vasculature or the lumen of the delivery system. In addition, it has a distal shape and arrangement of stiffness variations that cause the wire to "seat" or anchor itself in the target anatomy.

This guide wire in a preferred embodiment achieves these goals from several design features.

First, the guide wire of the preferred embodiment has 5 zones of differing stiffness. The distal tip or leading end is very floppy and atraumatic. The second zone, going proximal from the distal tip, is a transition zone going from floppy to semi-stiff. The third zone is a semi stiff region. The fourth zone is the body of the guide wire and is a very stiff segment. The fifth zone, at the proximal end is a transition zone from very stiff to semi-stiff at the proximal most end.

The second design feature of the preferred embodiment is a "J" curve in a floppy tip portion of the distal tip. The "J" shape provides a shape and leading end surface that minimizes the possibility of digging into the vessel wall.

The third design feature of the preferred embodiment is a large radius, secondary curve that incorporates the transition to semi-stiff zone, the semi-stiff zone and the distal part of the stiff or body portion. This secondary curve is sized to roughly fit the curvature of the aorta.

The fourth design feature of the preferred embodiment is an extremely stiff shaft or body portion that provides the strength to guide the interventional device.

The fifth design feature of the preferred embodiment is a transition from full stiffness to semi-stiff at the proximal end. The semi-stiff proximal portion provides the flexibility needed to allow the interventional delivery system to be loaded onto the wire and advanced without damaging the guide wire lumen or becoming jammed in the interior of the device.

BRIEF DESCRIPTION OF THE DRAWINGS

This then generally describes the invention but to assist with understanding of the invention reference will now be made to preferred embodiments with the assistance of the accompanying drawings.

FIG. 12 shows a further embodiment of an extra stiff guide wire according to the present invention;

FIG. 13 shows a detailed view of the distal end of the guide wire of FIG. 12;

FIG. 14 shows a detailed view of the proximal end of the guide wire of FIG. 12; and FIG. 15 shows a detailed view of the proximal end of an alternative embodiment of a guide wire according to the invention.

DETAILED DESCRIPTION

Figure 1:
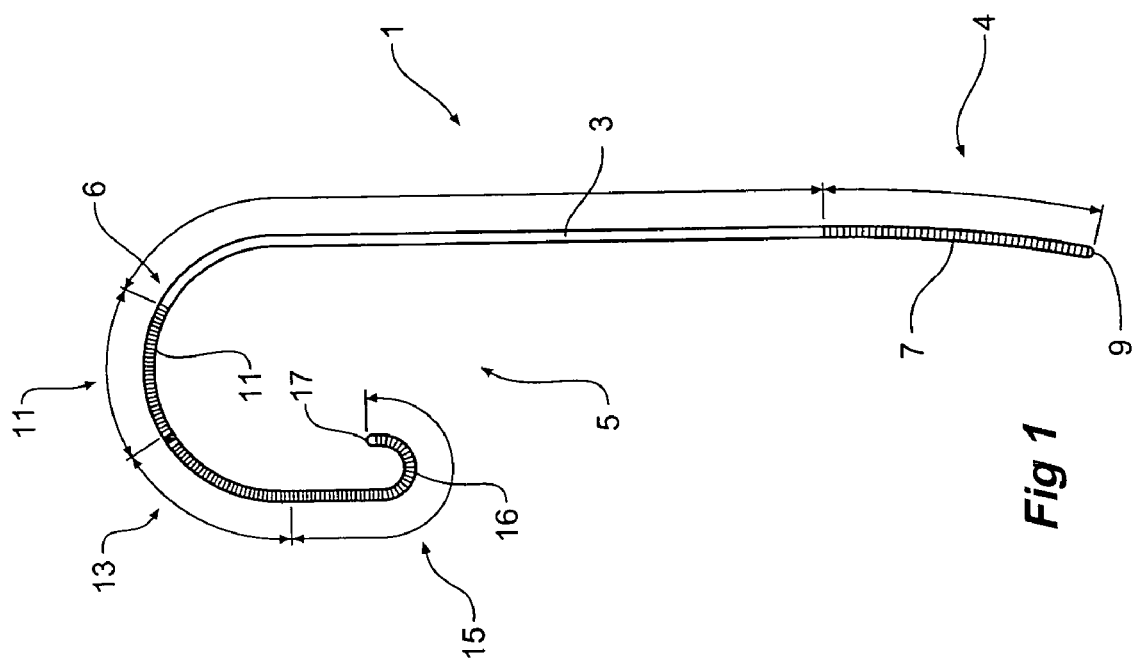
FIG. 1 shows a schematic view of a guide wire according to one embodiment of the present invention.

Now looking more closely at the drawings it will be seen that FIG. 1 shows the general layout of a guide wire according to one embodiment of the invention. The guide wire includes a combination of flexibilities, lengths of the flexible sections and the size and shape of the curves that together result in a guide wire that can be percutaneously introduced through a needle, advanced through the artery without damaging the artery, seat firmly in the anatomy when in place and not "poke" or irritate the aortic heart valve.

In FIG. 1, the guide wire generally shown as 1 includes a central zone 3, a proximal zone 4 and a distal zone generally shown as 5. The central zone 3 is of substantial stiffness to assist with the deployment of a stent graft deployment device. The proximal zone 4 ranges in stiffness from full stiffness adjacent to the central zone 3 down to a semi-stiff proximal end 9.

The distal zone 5 includes a first semi-stiff zone 11 which is a transition from full stiffness adjacent the central zone 3 to semi-stiff and then there is a transition zone 13 which has a transition from semi-stiff through to relatively flexible and then there is a flexible zone 15 which is highly flexible or floppy.

The distal zone 5 has a distal curve 6 which forms a substantial semicircle which encompasses part of the central zone 3 the semi-stiff zone 11 and part of the transition zone 13. The distal flexible zone has a small tip curve 16 in the form of a J terminating in a distal tip 17. The small tip curve 16 terminating in the distal end 17 in use as discussed above terminates near the aortic heart valve and the J tip prevents damage to the aortic heart valve.

Figure 2:
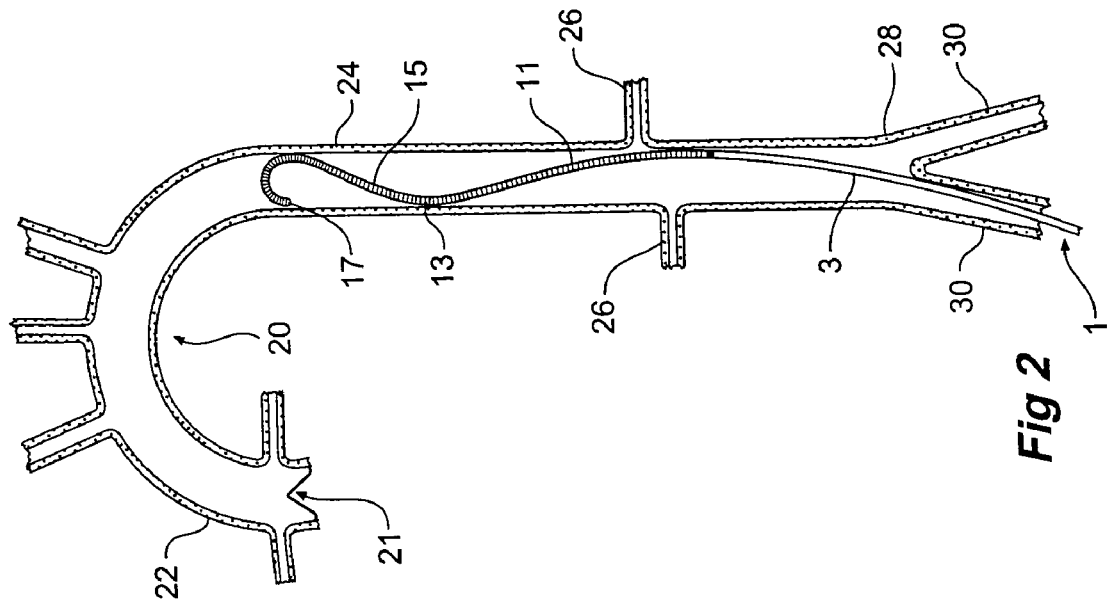
FIG. 2 shows a schematic view of an aorta of a patient incorporating a thoracic arch with the guide wire being introduced by a femoral route.

FIG. 2 shows the form of the wire as it is passing from the femoral artery at the entry site, up into the abdominal and thoracic aorta. Note that all contact points are large gentle radiuses and that there are no "kink" points at the changes in stiffness. Also, this combination of curves causes the guide wire to orient itself in such a way that the small distal curve always points away from the origins of the major branch vessels. This insures that the guide wire tip will not inadvertently exit into the wrong vessel.

FIG. 2 shows a schematic aorta of a patient with a guide wire according to the invention being deployed into it. The schematic aorta includes an aortic arch 20, an aortic heart valve 21, a ascending aorta 22 and a descending aorta 24. Down the descending aorta 24, there are renal arteries 26 and an aortic bifurcation 28 with two iliac arteries 30 extending to femoral arteries from the aortic bifurcation 28. The guide wire 1 is introduced into one of the femoral arteries by means of an incision (not shown) with the distal end 17 of the guide wire being introduced first and progressing up the femoral artery, through the iliac artery 30, past the aortic bifurcation 28 and into the descending aorta 24.

Figure 3:
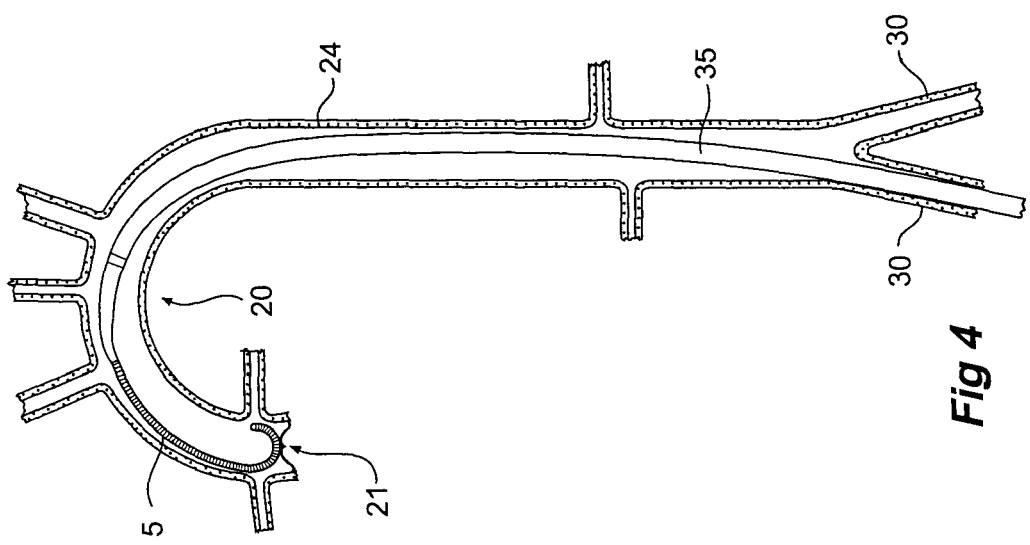
FIG. 3 shows the view of FIG. 2 with the guide wire introduced up to the thoracic arch.

FIG. 3 shows the guide wire in place. Note that the floppy distal J tip 16 seats on the aortic valve but does not present a point or kink to the valve surface. The large curve is re-formed and substantially follows the contour of the aorta. The stiff portion or body portion of the wire extends down through the thoracic and abdominal aorta and out the entry site in the femoral artery. The large curve firmly anchors the wire in the aorta so that as the delivery device is advanced, the guide wire will stay in place. As the delivery device is advanced, some of the forward pushing motion is transferred to the guide wire, this motion causes the distal tip of the guide wire to bump into the heart valve. The floppy curved tip can bump into the valve without causing damage and possible premature ventricular contractions (PVC).

As shown in FIG. 3, the guide wire 1 has been fully deployed into the thoracic arch 20 and at this stage the J tip 16 is adjacent the aortic valve 21 and the curve of the distal zone 5 approximates the curve of the thoracic arc and the main central zone 3 of the guide wire extends down the descending aorta 24.

Figure 4:
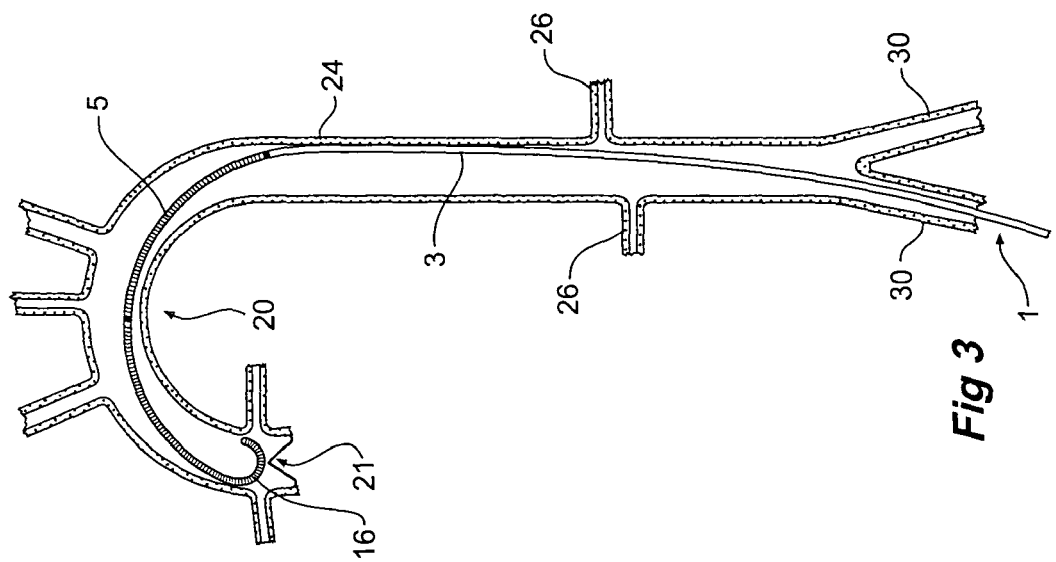
FIG. 4 shows the view shown in FIG. 3 with a deployment device introduced over the guide wire.

FIG. 4 shows the delivery or deployment device in place over the guide wire. The working portion of the delivery system is over the stiffest portion of the guide wire and the guide wire will control the location of the delivery device during the stent graft deployment.

As can be seen in FIG. 4, a delivery device generally shown as 35 has been deployed onto the guide wire and advanced up through the femoral and iliac arteries 30 into the descending aorta 24 and on up into the thoracic arch 20. The curve at the distal zone 5 assists in causing the deployment device to form into the shape of the thoracic arch 20 without unnecessary pressure being applied onto the walls of the aortic arch 20. Subsequently the various steps of deployment of a stent graft in the thoracic arch of a patient may be carried out and then the guide wire can be withdrawn.

Figure 5:
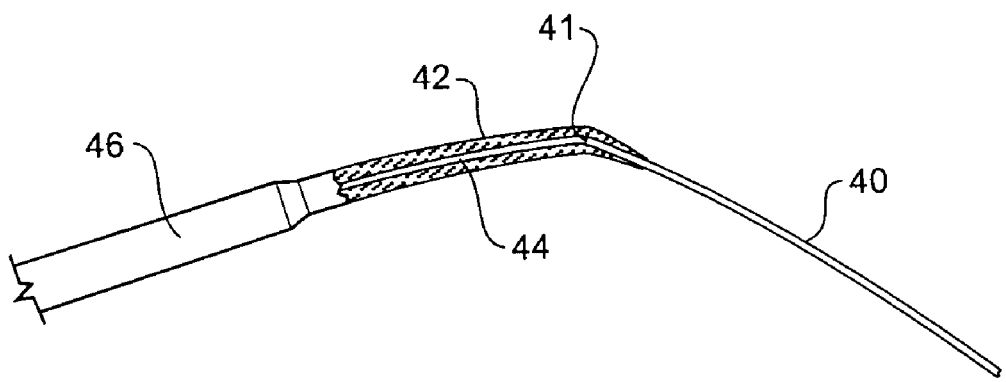
FIG. 5 shows the proximal most end of prior art guide wires of a type used for endovascular procedures introduced into the nose cone dilator of a deployment device.

FIG. 5 shows the proximal-most end of prior art guide wires of a type used for these procedures. Note that the proximal portion of the guide wire is as stiff as the body portion. Being stiff enough to control a large diameter delivery system, the proximal most end is like a "spear" and not easily inserted into the delivery devices. The distal ends of the delivery devices are typically fairly flexible, to help them negotiate the vasculature. If the stiff end of the prior art wires is not fed into the delivery system very carefully and monitored while being advanced, the hard, stiff proximal end will dig into and jam in the delivery system lumen.

FIG. 5 shows a prior art arrangement by which the proximal end 40 of a prior art guide wire is deployed into the lumen 44 of a nose cone dilator 42 of a deployment device 46. It will be noted that the sharp end 41 on the prior art wire guide 40 can jam in the nose cone dilator 42 and cause problems.

Figure 6:
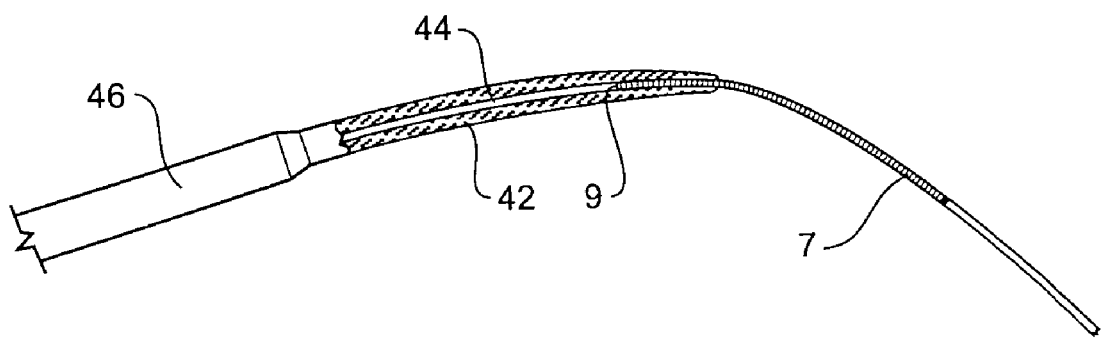
FIG. 6 shows the proximal most end of guide wires of the present invention used for endovascular procedures introduced into the nose cone dilator of a deployment device.

FIG. 6 shows the proximal most end of the guide wire of this invention. The semi-flexible area, with the transition to the stiff body section will conform to any misalignments between the long axis of the guide wire and the long axis of the delivery system allowing the delivery system to advance over the wire without worry of jamming or damage to the interior of the delivery system.

Hence as shown in FIG. 6, the proximal zone 7 with a transition from full stiffness to semi-stiffness is flexible enough to be fed through the nose cone lumen 44 of a nose cone dilator 42 of the deployment device 46 and the end 9 does not jam in the lumen 44.

Figure 7:
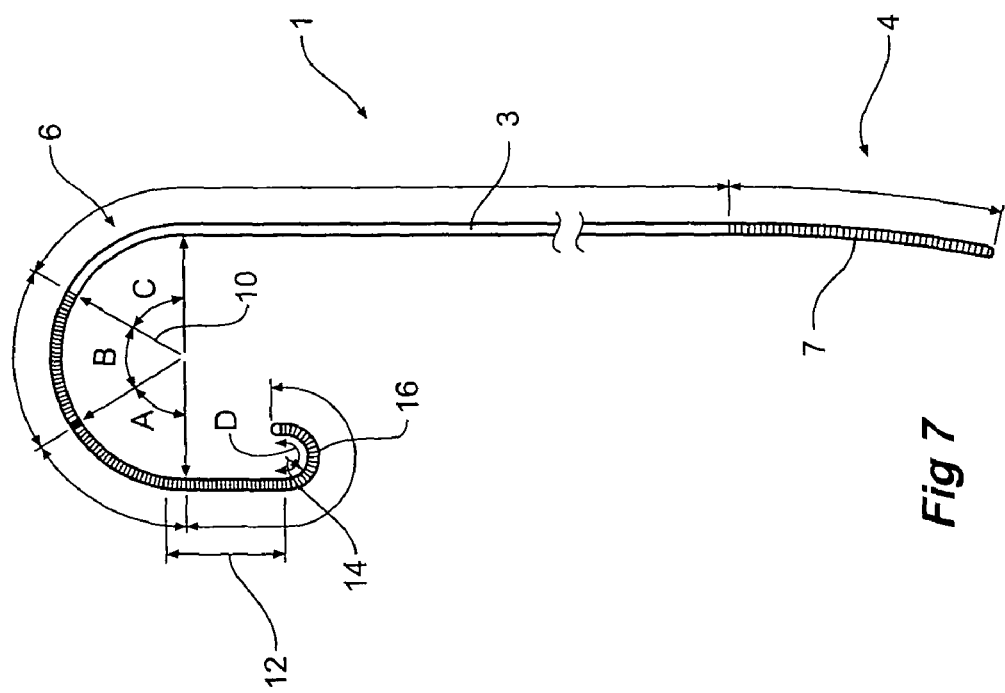
FIG. 7 shows a guide wire according to the present invention and particularly the preferable dimension of the various zones.

FIG. 7 shows a guide wire according to the present invention and particularly the preferable dimension of the various zones.

The overall length of the guide wire may be in the range of 250 to 300 cm and preferably 260 cm. The length of the tip curve 16 could be in the range of 3 cm to 15 cm, preferably in the range of 5 cm to about 10 cm, with a preferred length of about 7 cm. The radius 14 of the tip curve 16 could be in the range of 5 mm to 20 mm with the preferred embodiment at 10 mm. The distance 12 between the distal part of the distal curve 6 to the proximal part of the tip curve 16 could be in the range of 2 cm to 10 cm with the preferred being 5 cm. The radius 10 of the distal curve 6 could be in the range of 5 cm to 15 cm with the preferred being about 9 cm. The angle of the arc (D) made by the tip curve 16 could be in the range of 110 degrees to 270 degrees with the preferred being 180 degrees. The angle of the arc of the distal curve 6 (A+B+C) could be in the range of 140 to 200 degrees with the preferred being 180 degrees. The angle of the arc described by the floppy to semi-stiff segment of the distal curve 6 (angle C) could be in the range of 30 degrees to 70 degrees, with the preferred being about 60 degrees. The angle of the arc described by the semi-stiff portion of the distal curve 6 (angle B) could describe an arc of 40 degrees to 90 degrees with the preferred being 70 degrees. The angle of the arc described by the full stiff body portion of the distal curve 6 (angle A) could be 40 to 80 degrees with the preferred being 50 degrees. The relative lengths of portions of the distal curve that are full stiff (A), semi-stiff (B) and semi-stiff to floppy transition C) to the overall length of the distal curve are about 28% full stiff, 40% semi-stiff and 32% semi-stiff to floppy.

The proximal transition zone 7 from full stiffness to semi-stiff could range in length from 3 cm to 20 cm with the preferred being 8 to 10 cm.

Figures 8, 9:
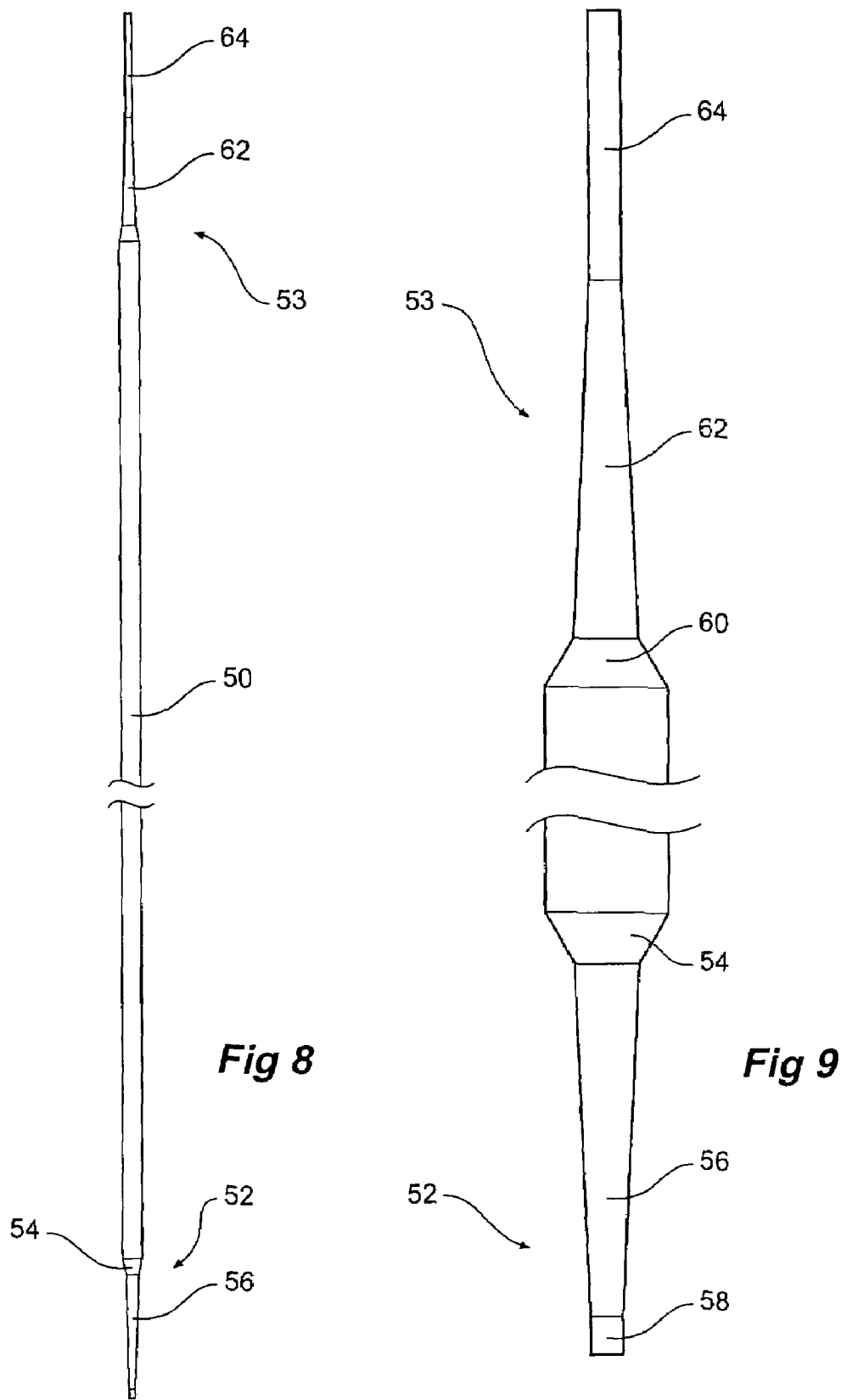
FIG. 8 shows a view of one embodiment of mandrel for the guide wire.
FIG. 9 shows detail of the embodiment shown in FIG. 8.

FIG. 8 shows a mandrel for the manufacture of a guide wire according to the present invention and FIG. 9 shows detail of the ends of the mandrel.

The mandrel includes an elongate stainless steel rod 50 which may have a diameter of between 0.5 to 1 mm and preferably approximately 0.8 mm. At the proximal end 52 of the mandrel, there is a short tapering transition zone 54 then a tapered proximal zone 56 of gradually reducing diameter and then a short parallel sided end piece 58. At the distal end 53 of the mandrel there is a short tapering transitional zone 60, a tapered portion 62 of gradually reducing diameter and a constant diameter portion 64.

Figure 10:
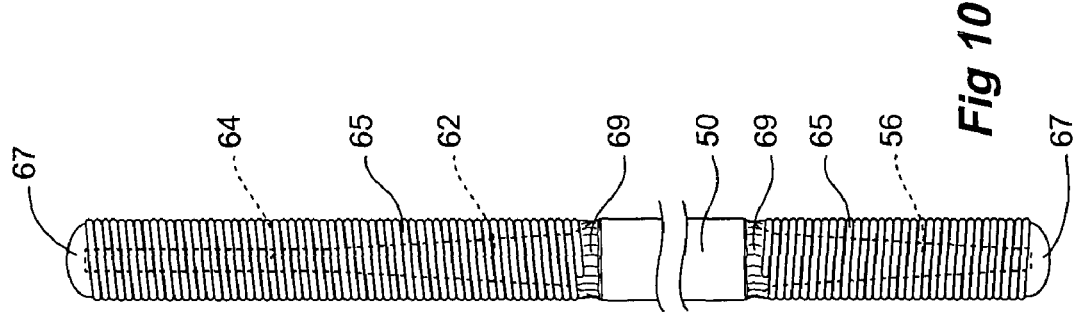
FIG. 10 shows detail of an assembled guide wire incorporating the mandrel of FIG. 8.

As can be seen in FIG. 10, a wire coil of substantially the same overall diameter as the central zone 50 is placed onto the proximal and distal zones. Each wire coil 65 is formed from a helix of wire and terminates in a rounded end 67. The coil is joined to the mandrel in the respective transition zones 54 and 60 by means of laser welding 69.

Figure 11:
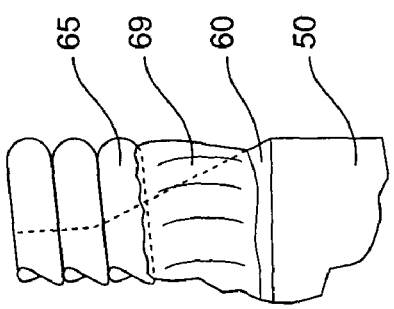
FIG. 11 shows detail of the laser welding between the mandrel and a wire coil.

FIG. 11 shows detail of the laser welding and it will be noted that the welding 69 forms a join between the wire 65 and the transition piece 60 of the mandrel but at no stage does the diameter get any greater than the overall diameter of the mandrel 50. This ensures that there is not a region of greater diameter than the diameter of the central zone 50.

Now looking at FIGS. 12 to 14 of the drawings it will be seen that a guide wire 70 of an alternative embodiment of the invention has a essentially straight and stiff portion 72 intermediate the proximal end 80 and the distal end 75. Towards the distal end 75 there is a pre-formed bend 73 which approximates the curve of the thoracic arch of a patient. The radius of curvature of this portion of the guide wire may be from five to fifteen centimetres.

At the distal tip 75 there is a less stiff flexible portion 76 terminating in a rounded distal tip 77 (see FIG. 13). The flexible portion 76 is formed into a pigtail or spiral so that as the guide wire is deployed within the vasculature of a patient the tip 77 does not engage against the wall of the artery or vasculature into which it is deployed to the extent that any damage to the wall of the artery or vasculature occurs.

At the proximal end 80 the substantially stiff portion 72 becomes more flexible in the region 74 and terminates in a proximal tip 82 which is rounded to facilitate its insertion into the guide wire lumen of a deployment device (see FIG. 14). It will be noted that the guide wire in the region 74 is of constant diameter but as indicated above it is more flexible. The guide wire at the proximal end 74 is illustrated in FIG. 12 as being curved but this is done to indicate that the proximal end is more flexible than the central portion 72. The proximal end of the guide wire 74 would, at rest, be essentially straight as can be seen in FIG. 14.

In FIG. 15 there is shown a detailed view of the proximal end of an alternative embodiment of a guide wire according to the invention. In this embodiment the proximal portion 90 is flexible and tapered so that the region has a diameter which changes from the diameter of the main body portion 92 to the smaller tip 96. Once again the tip 96 of the proximal end is rounded to facilitate its insertion into the guide wire lumen of a deployment device.

One method by which the flexible and tapered tips at the proximal end may be formed is by providing a coil of wire over a mandrel which has a diameter which decreases in direction towards the proximal end. The coil may be formed of a single helical wound wire which has a diameter which decreases from one end to the other with the large diameter beginning in a region closer to the central portion of the guide wire and the smaller diameter wire ending in a region closer to the distal or proximal end respectively. Alternatively, the guide wire may be formed from a solid metal wire which is drawn down in several stages to have a decreasing diameter towards the distal end and towards the proximal end. This solid metal wire may be surrounded by a flexible coil having a outer diameter which decreases towards the proximal end.

Other known methods may also be used to form guide wire and particularly the distal and proximal tips.

The guide wire of this invention may be manufactured with a central wire member or mandrel with a spring temper or high tensile strength. The central member has a taper on the distal end that produces certain parts of the flexibility changes as well as a taper on the proximal end that produces the stiffness transitions at the proximal end. The body or stiff portion of the guide wire may be a spring temper or high tensile strength thin walled tube. This tube is place primarily over the un-tapered, full diameter portion of the central wire. A spring coil is placed over the distal tapered portion of the central wire to maintain the diameter of the guide wire at the tapered portion. In addition, a thin high tensile strength ribbon wire may be incorporated in the interior of the spring coil to aid in producing the correct transitions and to anchor the distal most part of the spring coil to the body of the guide wire to prevent the spring coil from elongating during retraction from the patient. A spring coil is also added to the proximal end of the coil to maintain diameter at the tapered proximal portion and to provide the correct flexibility to allow the wire to pass into delivery devices smoothly. Solder or braze joints are placed strategically along the distal coil to anchor the coil to the central member and aid in supplying the correct stiffness transition. This may be accomplished by compressing the coils in the semi-stiff portion during the soldering or brazing operation while the coil is in a straight condition. The resulting "pre-load" on this segment of coils makes the segment stiffer than a non-compressed coil section but more flexible than the body portion.

The entire guide wire can be made of high tensile stainless steel materials such as ANSI type 304LVM at 350,000 to 400,000 psi tensile strength. Other materials or combinations of materials could be used such as Nitinol, Tungsten, MP35N, cobalt chrome, etc. The various connections in the guide wire assembly can be made by brazing, soldering, arc welding, laser welding, glue bonds, etc.

The present invention is useful in the performance of vascular surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A guide wire to assist percutaneous endovascular deployment within a thoracic arch region of an aorta, the guide wire having zones of varying stiffness comprising:
   a proximal end and a distal end;
   a proximal zone adjacent the proximal end and having a semi-stiff proximal portion, a distal portion of high-stiffness, and a transition portion transitioning from the semi stiffness of the proximal portion to the high stiffness of the distal portion, the proximal zone having a length of from 5 cm to 20 cm;
   an elongate central zone of high stiffness adjacent to the proximal zone having a substantially constant diameter along its length;
   a distal zone adjacent to the high stiffness central zone and having a proximal portion of high-stiffness adjacent to the distal portion of the central zone and transitioning to a distal portion of highest flexibility wherein the distal zone comprises a first pre-formed curve with a radius of curvature of from 5 cm to 15 cm and being comprised of three zones:
- a semi stiff zone having a proximal portion abutting, and having a stiffness equivalent to the distal portion of the central zone transitioning to a distal portion of semi-stiffness;
- a transition zone having a semi-stiff proximal portion adjacent to the distal portion of the semi stiff zone transitioning to a flexible distal portion; and
- a flexible zone having a flexible proximal portion adjacent to the distal portion of the transition zone transitioning to a distal portion of least stiffness and highest flexibility having an atraumatic and highly flexible pre-formed tip curve having a single direction of curvature with a radius of curvature of from 5 to 20 mm, the high flexibility and the direction and radius of curvature being selected so that the tip curve can contact the aortic valve without penetrating or causing damage to the valve and a coil extending from the semi-stiff zone to a distal portion of the distal zone.

2. A guide wire as in claim 1 wherein the central zone comprises a stainless steel mandrel.

3. A guide wire as in claim 1 wherein the proximal zone comprises a tapered mandrel with a proximal wire coil of substantially constant coil diameter on and extending along the tapered mandrel.

4. A guide wire as in claim 3 wherein the proximal wire coil is laser welded to the tapered mandrel.

5. A guide wire as in claim 3 wherein the proximal wire coil terminates in a rounded tip.

6. A guide wire as in claim 1 wherein the distal zone comprises in order from the central zone, a tapered mandrel portion and a portion of constant reduced diameter with a distal wire coil of substantially constant coil diameter on and extending along the tapered mandrel portion and the portion of constant reduced diameter.

7. A guide wire as in claim 6 wherein the distal wire coil is laser welded to the tapered mandrel portion.

8. A guide wire as in claim 6 wherein the distal wire coil terminates in a rounded tip.

9. A guide wire as in claim 1 wherein at least some portions of the guide wire are radio-opaque.

10. A guide wire as in claim 1 wherein the proximal zone comprises a proximal wire coil of substantially constant diameter and the distal zone comprises a distal wire coil of substantially constant coil diameter and the central zone, the proximal wire coil and the distal wire coil are coated with polytetrafluoroethylene.

11. A guide wire that has a stiffness to control large diameter, stiff devices but still not damage the aortic valve or the lumen of the delivery system, wherein the guide wire has five zones of differing stiffness, the guide wire comprising:
- a proximal end and a distal end;
- a first zone adjacent to the distal end and having a distal portion terminating in a distal pre-formed tip curve having the highest flexibility and having a single direction of curvature with a radius of curvature of from 5 to 20 mm, the high flexibility and the direction and radius of curvature being selected so that the tip curve can contact the aortic valve without penetrating or causing damage to the valve transitioning to a flexible proximal portion;
- a second zone having a flexible distal portion adjacent to the proximal portion of the first zone transitioning to a semi-stiff proximal portion;
- a third zone having a semi-stiff distal portion adjacent to the proximal portion of the second zone transitioning to a proximal portion of high stiffness, wherein the first, the second, and the third zones have a pre-formed curve shape;
- a fourth zone having a distal portion abutting, and having a stiffness equivalent to the proximal portion of the third zone and a proximal portion of high-stiffness; and
- a fifth zone having a distal portion of high-stiffness adjacent to the proximal portion of the fourth zone transitioning to a semi-stiff proximal portion adjacent to the proximal end and having a length of from 5 cm to 20 cm and a coil extending from the third zone to a distal portion of the first zone.

12. A guide wire according to claim 11, having a "J" curve in a floppy tip portion of the distal tip curve, which provides a shape and leading end surface that minimizes the possibility of digging into the vessel wall.

13. A guide wire according to claim 11, having a transition from full stiffness to semi-stiff at the proximal end, the semi-stiff proximal portion providing flexibility to allow the interventional delivery system to be loaded onto the wire and advanced without damaging the guide wire lumen or becoming jammed in the interior of the device.

14. A guide wire according to claim 11, wherein the first and fifth zones are coated with polytetrafluoroethylene.

15. A guide wire according to claim 11, wherein the first zone terminates in a rounded tip at the proximal portion.

16. A guide wire according to claim 11, wherein at least some portions of the zones are radio-opaque.

* * * * *